(12) United States Patent
Granados

(10) Patent No.: US 6,403,375 B1
(45) Date of Patent: Jun. 11, 2002

(54) ESTABLISHMENT OF *TRICHOPLUSIA NI* CELL LINES IN SERUM-FREE MEDIUM FOR RECOMBINANT PROTEIN AND BACULOVIRUS PRODUCTION

(75) Inventor: Robert R. Granados, Ithaca, NY (US)

(73) Assignee: Boyce Thompson Institute for Plant Research, Inc., Ithaca, NY (US)

( * ) Notice: Subject to any disclaimer, the term of this patent is extended or adjusted under 35 U.S.C. 154(b) by 0 days.

(21) Appl. No.: 08/294,953

(22) Filed: Aug. 24, 1994

(51) Int. Cl.[7] .................................................. C12N 5/00
(52) U.S. Cl. ....................................................... 435/348
(58) Field of Search ......................... 435/240.2, 240.21, 435/240.23, 240.3, 240.31, 172.1, 948, 348, 383, 404, 325

(56) References Cited

U.S. PATENT DOCUMENTS 5,348,877 A * 9/1994 McKenna et al. .......... 435/325

* cited by examiner

*Primary Examiner*—Leon B. Lankford, Jr.
(74) *Attorney, Agent, or Firm*—Brown & Michaels, PC

(57) ABSTRACT

This disclosure presents the establishment of new cell lines from *Trichoplusia ni* eggs, in a commercial serum-free medium. These new cell lines were screened with wild-type *Autographa californica* multiple nuclear polyhedrosis virus (AcMNPV) and *Trichoplusia ni* single nuclear polyhedrosis virus (TnSNPV). In addition, selected cell lines from the initial screenings with the native baculoviruses, were further tested for their capacity to express recombinant proteins.

10 Claims, 2 Drawing Sheets

US 6,403,375 B1

ESTABLISHMENT OF *TRICHOPLUSIA NI* CELL LINES IN SERUM-FREE MEDIUM FOR RECOMBINANT PROTEIN AND BACULOVIRUS PRODUCTION

REFERENCE TO RELATED APPLICATIONS

This patent application is related to the following patent applications and patents:
1) U.S. Pat. No. 5,300,435, granted Apr. 5, 1994, entitled "*TRICHOPLUSIA NI* CELL LINE WHICH SUPPORTS REPLICATION OF BACULOVIRUSES";
2) U.S. Pat. No. 5,298,418, granted May 29, 1994, entitled "CELL LINE ISOLATED FROM LARVAL MIDGUT TISSUE OF *TRICHOPLUSLA NI*";
3) U.S. Pat. No. 5,348,877, granted Sep. 20, 1994, entitled "METHOD OF ADAPTING ANCHORAGE-DEPENDENT CELL LINES TO SUSPENSION CONDITIONS".

FIELD OF THE INVENTION

The invention pertains to the field of insect cell lines. More particularly, the invention pertains to *Trichoplusia ni* cell lines established in serum-free medium.

BACKGROUND OF THE INVENTION

Since Grace (1962) established the first insect cell line, insect cell culture has been progressing at a rapid rate. Insect cells have been used successfully to produce recombinant proteins, pharmaceutical and new biopesticides, due to the development of the baculovirus expression vector system (BEVS) (Ribeiro and Crook, 1993). This system utilizes the strong polyhedrin and p10 promoters (Miller, 1988) to produce large amounts of protein. To date, more than 200 foreign genes from viral, bacterial, invertebrate, mammalian and plant species have been expressed successfully with the BEVS. However, cell lines derived from different insect species differ in their ability to produce virus or express recombinant proteins. Furthermore, culture conditions and media type play major roles in choosing the appropriate cell line and system for a particular application.

One of the insect cell lines which has shown great promise is BTI-Tn-5B1-4, established at Boyce Thompson Institute, Ithaca, N.Y. and commercially available as High Five™ cells from Invitrogen Corp. The cell line is on deposit at the American Type Culture Collection as ATCC CRL 10859. This novel cell line is the subject of U.S. Pat. No. 5,300,435, granted Apr. 5, 1994. These cells were derived from eggs of the Cabbage Looper (*Trichoplusia ni*). They have been found to be particularly susceptible to baculoviruses, which are adaptable to genetic modifications which lead to high levels of production and secretion of proteins.

Recent data suggests that different insect cell lines differ in their capacity to produce occlusion bodies (OBs) and recombinant proteins. It has been previously reported that BTI-Tn-5B1-4 (Tn-5B1) cells produced a minimum for 20-fold more secreted alkaline phosphatase (SEAP) on a per cell basis than the IPLB-Sf-21 (Sf-21) cell line derived from *Spodoptera frugiperda*.

Along with the development of baculovirus expression vectors, the development of serum-free media (SFM) for the growth of insect cells and for virus replication, has become critical to the success of large-scale production operations. The primary reasons for this are the high cost of fetal bovine serum (FBS) and the various components of FBS that make the downstream purification and recovery process difficult.

At present, most of the attention is being focused on the adaptation of cell lines to serum-free media and the development of new serum-free media which will broadly support the replication of baculoviruses and the expression of recombinant proteins. One approach has been to investigate the use of commercial serum replacements in place of serum.

Stiles et al. (1992) recently established the first Coleopteran cell lines in serum-free medium; however, no information on the cell lines ability to support the replication of baculoviruses and express recombinant proteins was reported. While this was the first known invertebrate cell line to be established in serum-free medium, it was unknown whether an attempt to establish a Lepidopteran cell line in serum-free medium would be successful. Those skilled in the art have always believed that it is necessary to establish cell lines in medium containing serum and then adapt the cell lines to serum-free conditions.

SUMMARY OF THE INVENTION

New cell lines from the cabbage looper, *Trichoplusia ni*, have been established in a commercially-available, serum-free medium.

The cell lines were screened with, and found to be susceptible to, AcMNPV-1A and TnSNPV. Selected cell lines demonstrating superior growth qualities and virus susceptibility were chosen for further screening. A cell line designated BTI-Tn4B (Tn4B) and a daughter cell line designated BTI-Tn4B31, produced more occlusion bodies per cell than any other cell line tested and were approximately three-fold more productive than IPLB-Sf-21 cells. Bioassay results showed that the occlusion bodies produced in Tn4B cells were more infectious than those derived from IPLB-sF-21 cells and *T.ni* larvae. To evaluate the expression capacity of the new cell lines for recombinant protein, two recombinant AcMNPV viruses, E2-β-Gal and AcSEAP, were used and compared with IPLB-SF-21 and another *T.ni* cell line, BTI-Tn-5B1-4, available through Invitrogen under the trademark, High Five™, which is known to express recombinant proteins at high levels. Under the same conditions, β-galactosidase and alkaline phosphatase production in two cell lines—Tn4B and Tn4B31—produced more of these proteins than IPLB-Sf-21 cells, but were not significantly different from BTI-Tn-5B1-4 cells.

The establishment of these new cell lines in serum-free medium is a great step forward in the art of insect cell lines. The new cell lines make the cost of producing recombinant proteins and large scale quanities of viral pesticides much less expensive. This decrease in production expenses is an important step towards more economical and safer insect control.

More advantages and features of the new cell lines will become apparent from the drawings and following detailed description.

DESCRIPTION OF THE PREFERRED EMBODIMENT

Figure 1:
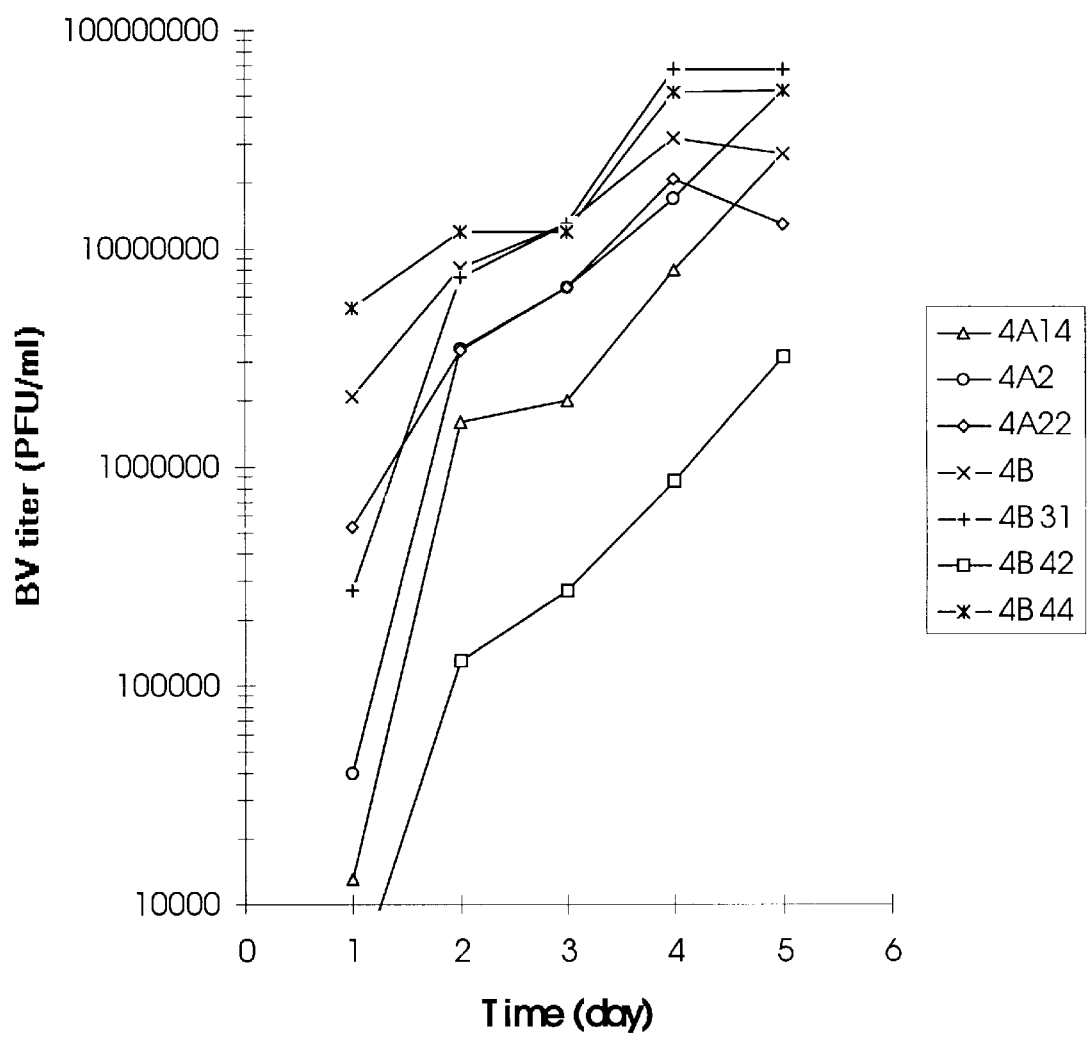
FIG. 1 shows an AcMNPV-1A BV growth curve in the new cell lines in serum-free medium.

The cabbage looper, *Trichoplusia ni*, is a very important agricultural pest worldwide. This insect is very sensitive to several baculoviruses. Recently, a new cell line, Tn-5B1-4, which was established from *T. ni* eggs in serum-containing medium, was determined to be superior to all other cell lines—Sf-21 and Sf-9—for β-galactosidase production (Wickham et al., 1992) and SEAP expression (Davis et al., 1992).

At present, the majority of studies involving the baculovirus expression vector system (BEVS) utilize established cell lines, such as Sf-21, Sf-9, Tn-368 and Tn-5B1-4. All these cell lines were established in serum-containing media. In order to demonstrate that serum-free media can replace serum-containing media for baculovirus production and recombinant protein expression, Hink (1991), Wang et al. (1992), and Chen et al. (1993), tested the capacity of commercially available serum-free media to support baculovirus replication and the expression of β-galactosidase in Sf-21, Sf-9, Tn-368, and Bm5 cell lines.

However, until the present invention, Stiles et al were the only scientists known to have established an insect cell line in serum-free medium. Initially, thirty one cell lines were established from *Trichoplusia ni* eggs as described by Granados et al. (1986) wherein said methods are incorporated herein by reference.

In general, after initiation of primary, embryonic cell cultures using the procedure outlined in Table 1, cultured cells will begin dividing within 4 to 10 days., and the first subculture will be possible within 2–3 weeks.

TABLE 1
Procedure For Establishment of New Embryonic Cell Lines From Lepidopterous Eggs
1. 300–400, 24-hour-old eggs are sterilized in 2% chlorox, 70% ethanol, and rinsed in GTC-100 tissue culture medium
2. With a rubber policeman the eggs are crushed through a 100 mm sieve into fresh medium
3. The homogenate is centrifuged at 200 g for 5 minutes and the pellet resuspended in 5 ml of TNM-FH tissue culture medium
4. The cells are seeded into 25 cm$^2$ tissue culture flask and incubated at 28° C.

The following procedure for the screening of novel cell lines for susceptibility to *Autographa californica* multiple nuclear polyhedrosis virus (AcMNPV) and expression of model recombinant viruses was used successfully.

1. The donor insect species for new cell lines is usually one whose larval stage is highly susceptible to AcMNPV. Also, the insect species should have a relatively short life cycle and be easily reared on artificial diet. Examples of such insect species include; *T. ni, S. Frugiperda, Plutella xylostella,* and *Anticarsia gemmatalis*.
2. New cell lines are subcultured in serum-containing medium for 15–20 passages in 25 cm$^2$ T-flasks prior to initial testing. During this time, cell cultures are selected for properties such as their ability to grow as anchorage-dependent or suspension cultures and short doubling time.
3. The cell lines, prior to forming a monolayer, are screened for susceptibility to AcMNPV by inoculating cells in multiwell plates (duplicate wells per cell line) at a multiplicity of infection (MOI) of 10 plaque-forming units (pfu) per cell. Other viruses can also be tested at this time. Infection levels are determined by phase contrast examination of the inoculated cells at 2–3 days postinoculation and counting the percentage of cells containing polyhedra or occlusion bodies (OBs).
4. Since it is well known that some cell lines may support OB formation with little or not occlusion of infectious virions, it is important to conduct larval bioassays with OBs purified from infected cells. This step is important if the main goal is to select cell lines for production of viral pesticides.
5. Cell lines that exhibit over 90% susceptibility to AcMNPV and are infectious to larvae are selected for further screening, and three to six ampules of each selected cell line are frozen in liquid nitrogen. The remaining lines are discarded. At this time (after about 30 passages) selected cell lines are adapted to serum-free media. Depending on the cell lines, adaptation to a serum-free medium could take an additional 5–20 passages.
6. Screening of cell lines for virus and/or recombinant protein production usually will occur at about passages 40–50. A similar method can be used for evaluating OB production in selected insect cell lines.
7. Following step 6, only the high producing cell lines are kept and 10–15 ampules are stored in liquid nitrogen. The remaining cell lines are discarded.
8. Cell lines can be further improved and stabilized if they are cloned. This step will require re-evaluation of the cloned cell lines to produce high levels of virus or recombinant proteins. Further characterization of the lines would include isozyme analysis, karyotyping, determining cell doubling times, and growth curve analysis.

All cell lines were established and maintained in EX-CELL 400™ serum free medium (JRH Biosciences) in 25 cm$^2$ tissue culture flasks at 28° C. The Sf-21 cells and the Tn-5B1-4 Cells were adapted to EX-CELL 400™ serum free and subcultured for more than 200 and 100 passages, respectively. These cell lines were used as controls in all experiments.

These 31 original cell lines were screened for virus replication and seven cell lines were selected tor further screening. Each cell line was grown in serum free medium to mid-log growth phase, at which point the cells were seeded into 24 well plates (Falcon) at a density of 2×10$^5$ cells/ml (0.5 ml/well, final volume). The cells were allowed to attach overnight at 28° C. Spent medium was removed from each well, followed by inoculation with 0.5 ml fresh serum free medium containing AcMNPV-1A or TnSNPV BV at a multiplicity of infection (MOI) of 5 PFU/cell. The wild type viruses used for this screening are described below:

AcMNPV-1A Budded Virus

Second passage AcMNPV-1A budded virus (BV) was produced in Sf-21 cells in TNM-FH medium (Hink, 1976), following the inoculation of cells with infectious hemolymph from *T. in* larvae infected with AcMNPV-1A (Wood, 1980) occlusion bodies (OBs). The resulting infectious medium was subsequently used as inoculum. The virus titer was determined by plaque assay as described by Wood et al., (1977), using Sf-21 cells in TNM-FH medium.

TnSNPV Budded Virus

Second passage TnSNPV-BV was produced in Tn-5B1-4 cells inoculated with infectious hemolymph prepared from *T. ni* larvae. The virus titer was determined by the same plaque assay method described above, however, Tn-5B1-4 cells were used instead of Sf-21 cells.

All infections were incubated at 28° C. The percent infection was determined by the presence or absence of occlusion bodies at 24 hr intervals. For AcMNPV-1A infections, counts were taken from the 3rd day to the 5th day p.i. All virus screens were repeated 2–3 times each. Those cell lines demonstrating a higher percent infection rate were selected for further study.

Cells were seeded as above at a density of $1 \times 10^5$ cells/ml in 24 well plates and allowed to attach for 2–3 hours. At this point, the old medium was drawn off and 0.5 ml fresh medium containing AcMNPV-1A or TnSNPV BV (MOI=5) was added. After 6 days p.i. at 28° C., the percent infection was determined by the presence or absence of OBs in the nucleus. Purification and quantification of OBs were as described by Wang et al. (1992).

All the cell lines tested were sensitive to both AcMNPV-1A and TnSNPV. Polyhedra could be seen at 72 hours p.i. with AcMNPV-1A and at 96 hrs p.i. with TnSNPV. The infection percentage, however, was observed to be different in the different cell lines. Based upon this data, 7 cell lines were selected which were highly sensitive to both AcMNPV-1A and TnSNPV for OB production and expression of recombinant proteins.

Occlusion body production in the selected cell lines is summarized in Table 2. Sf-21 cells grown in EX-CELL 400™ serum free medium for more than 200 passages were used as controls for AcMNPV-1A whereas Tn-5B1-4 cells were used as controls for TnSNPV infections. The greatest numbers of AcMNPV-1A OBs were produced by Tn-4B, Tn-4B44, and Tn4B31 cells, however, more TnSNPV OBs were produced by Tn-4B and Tn4A14 cells. There are 4 cell lines which can produce more OBs than Sf-21 cells. Occlusion bodies were readily seen in the nuclei of the infected cells.

TABLE 2

Occulusion body production in new *Trichoplusia ni* cell lines in serum free meduim

| Cell Lines | AcMNPV-1A Production OBs($1 \times 10^6$)/ml | AcMNPV-1A Prodution OBs/cell | TnSNPV Production OBs ($1 \times 10^6$)/ml | TnSNPV Production OBs/cell |
|---|---|---|---|---|
| 4A14 | 14.7 | 38.1 | 181.50 | 1146 |
| 4A2 | 4.6 | 37.5 | 66.33 | 488 |
| 4A22 | 2.7 | 27.6 | 68.83 | 546 |
| 4B | 6.9 | 94.4 | 199.83 | 1135 |
| 4B31 | 8.5 | 53.8 | 146.00 | 869 |
| 4B42 | 7.7 | 50.1 | 84.83 | 757 |
| 4B44 | 14.7 | 85.9 | 109.95 | 901 |
| Sf-21 | 5.8 | 31.5 | 0 | 0 |

Further screenings revealed that the selected cell lines could support the replication of AcMNPV-1A and TnSNPV (Table 2). Of the seven cell lines tested, Tn4B produced more OBs than all other cell lines, including Sf-21 cells adapted to serum-free medium. Average OB production by Tn4B was three fold higher than Sf-21 cells in serum free medium (Table 1).

Figure 2:
FIG. 2 shows total β-galactosidase production at five days post infection in the new cell lines plus control cell lines IPLB-Sf-21 and BTI-Tn5B1-4, at cell densities of $2 \times 10^5$ cells/ml.

AcMNPV-1A-BV production in the different cell lines were similar as shown in FIG. 2. Maximum titers for all cell lines were reached by 96 hours post infection Mid-log phase cells were adjusted to $2 \times 10^5$ cells/ml with fresh medium, seeded into 24 well plates, and allowed to attach overnight. After the spent medium was removed, 0.1 ml AcMNPV-1A-BV (MOI-5), was added to each well. Infections were conducted by rocking each plate for 2 hr at 28° C. Following removal of the inoculum, the cells were washed twice with fresh serum free medium and re-incubated at 28° C. with 0.5 ml fresh medium in each well. Infectious medium was collected from 1 well for each cell line at 24 hours intervals. The viral titer (i.e., PFU/ml) was determined for each cell line using SF-21 cells as described above.

Bioassay data indicated that the infectivity of OBs from Tn4B did not differ from larval-derived OBs, but was higher than Sf-21 derived OBs in serum-free medium (Table 3). Occlusion bodies derived from the seven new cell lines and Sf-21 cells in serum free medium, and control OBs derived from *T. ni* larvae infected with AcMNPV-1A per os, were tested for virulence using the droplet feeding assay with *T. ni* neonate larvae (Hughes and Wood, 1981; Hughes et al., 1986). Briefly, the OBs were counted using a hemacytometer and adjusted to $1 \times 10^6$ OBs/ml in sterile water containing blue food coloring (FD&C Blue No. 1, 10 mg/ml). Thirty larvae were used for each treatment. The bioassays were repeated three times and the resulting data was analyzed by the student test.

TABLE 3

Bioassay results from AcMNPV-1A OBs derived from new *Trichoplusia ni* cell lines in serum free medium at $1/10^6$ OBs/ml

| Cell Lines | % Morality Exp. #1 | % Morality Exp. #2 | % Morality Exp. #3 | Average % Mortality ±SE |
|---|---|---|---|---|
| 4A14 | 70.0 | 63.3 | 60.0 | 64.4 ± 1.67 |
| 4A2 | 70.0 | 80.0 | 83.3 | 77.7 ± 2.25 |
| 4M2 | 66.3 | 66.7 | 63.3 | 64.4 ± 0.64 |
| 4B | 83.3 | 83.3 | 86.7 | 84.4 ± 0.64 |
| 4B31 | 60.0 | 70.0 | 76.7 | 68.9 ± 2.83 |
| 4B42 | 50.0 | 60.0 | 73.3 | 61.1 ± 3.87 |
| 4B44 | 36.7 | 36.7 | 30.0 | 34.5 ± 1.27 |
| Sf-21 | 63.3 | 53.3 | 56.7 | 57.8 ± 1.87 |
| Larvae | 83.3 | 73.7 | 90.0 | 82.2 ± 2.83 |

The virulence of the OBs produced by each cell line was compared with that from IPLB-Sf-21 cells in *T. ni* larvae. The results (Table 3) showed that the infectivity of OBs from *T. ni* larvae were not much different from cell line derived OBs except for the Tn-4B44 cell line. Note that the virulence of OBs from Tn-4B cells were higher than OBs from Sf-21 cells in serum-free medium, and, higher than the OBs from *T. ni* larvae. This is an important advantage of the cell lines of the present invention. Not only will the cell lines allow the cheaper production of viral pesticides, but the pesticides will be more virulent.

In other studies, using the baculovirus expression vector system, β-galactosidase is most commonly used to test expression levels of recombinant viruses in insect cell culture. Previous studies have demonstrated that Sf-9 and Tn-5B1-4 cells reach high levels of expression of β-galactosidase. Recently, Davis et al. (1992) constructed a recombinant baculovirus, AcSEAP, which was expressed at higher levels in Tn-5B1-4 cells (Davis et al., 1992; Davis et al., in press). This virus construct enables the researcher to examine both the expression and secretion of product from particular cell lines. The recombinant virus used to examine protein expression within the cell lines are described below:
E2-β-gal The recombinant AcMNPV containing the *Escherichia coli* β-galactosidase gene fused to the polyhedrin gene, was obtained from MicroGenesys (Wickham et a., 1992). Third passage virus was used in this study. The virus titer was determined by plaque assay (Wood, 1981) using Sf-21 cells. Blue plaques were counted using an Olympus IMT-2 inverted microscope at five days post infection (p.i.).

AcMNPV-SEAP

The recombinant virus clone expressing secreted alkaline phosphatase (SEAP) was isolated by Davis et al. (1992).

Third passage virus was used in this study. The virus titer was determined by plaque assay as described above. Plaques were counted following staining with 0.5% neutral red (Sigma).

The expression of two different recombinant proteins in the seven new *T ni.* cell lines was compared to the widely-used Sf-21 and Tn-5B 1-4 cell lines. For β-galactosidase production, Tn-5B1-4 cells reached expression levels as shown in FIG. 2; but for SEAP, two new cell lines, Tn4B and Tn4B31, reached higher activity levels than Tn-5B1-4 and Sf-21 (Tables 4 & 5). These results show that methods of establishing those cells lines using commercially available serum-free medium, EX-CELL 400™, work to establish insect cell lines, but can be used to establish insect cell lines that support wild-type and recombinant baculovirus replication.

Production and Assay of β-galactosidase

All cells were seeded at a density of $2\times10^5$ cells/ml in 24 well plates (0.5 ml/well, final volume) and allowed to attach for 2–3 hrs. After removal of the spent medium, the cells were inoculation with the E2-β-gal recombinant virus (MOI=10) and centrifuged at 1,000×g for 1 hr. The inoculum was removed and replaced with 0.5 ml fresh serum free medium. After six days p.i., both the cells and medium were collected and sonicated for 20 sec at 130 watts (Heat Systems-Ultrasonics, Inc., Plainview, N.Y.) to release the intracellular β-galactosidase activity was measured on the basis of the rate of cleavage of o-nitrophenyl B-D-galactopyranoside (ONPG) (Sigma) as described by Miller (1972). Briefly, samples were added to 0.8 ml of Z-buffer (60 mM $Na_2HPO_4$-$7H_2O$, 40 mM $NaH_2PO_4$-$H_2O$, 10 mM KCl, 1 mM $MgSO_4$-$7H_2O$, 50 mM B-mercaptoethanol) and incubated at 28° C. for 10 min. Following this, 200 ml ONPG (4 mg/ml) was added and the mixtures were incubated at 28° C. for 2 min. The reaction was stopped with 0.5 ml 1 M $Ma_2CO_3$, and the $OD_{420}$ of the solution was measured using a DU-64 Spectrophotometer (Beckman Instruments, Inc.). The following equation was used to calculate the β-galactosidase concentration in International Units per milliliter (IU/ml) using an extinction coefficient of 4.5 ml/mol for o-nitrophenyl:

$$IU/ml = (OD_{420})(1500ml)/(4.5\ ml)(incubation\ time)(sample\ vol.)$$

The seven new cell lines were infected with AcMNPV recombinant, E2-β-Gal, and compared to Sf-21 and Tn-5B1-4 cells. The cytopathic effect (CPE) was evident in >90% of the cells in all cell lines tested, however, no OBs were seen in the nucleus. β-galactosidase activity varied in the different cell lines, even though we maintained the same cell density, MOI, and the same infection conditions. β-galactosidase production in Tn-4B and Tn-4B31 cells were higher than all other cell lines including Sf-21, but was not higher than the Tn-4B1-4 cells, which are known to be superior to many other cell lines in β-galactosidase expression (Wickham et al., 1992).

Production and Assay of SEAP

Each cell line was infected with the Ac-SEAP recombinant virus in the same manner as described above for β-galactosidase. After 6 days p.i., both the medium and cells were collected and sonicated for 20 sec. Secreted alkaline phosphatase was assayed following the method of McComb and Bowers (1972) as modified by Davis et al. (1992). Briefly, samples were heated at 65° C. for 5 min to inactivate endogenous alkaline phosphatase. Afterwards, 2ml of sample was mixed with 200 ml of SEAP assay buffer (1 M diethanolamine, 0.5 mM $MgCl_2$, 10 mM homoarginine) in each well of a 96 well plate (Corning Inc., Corning, N.Y.), and incubated at 37° C. for 10 min. Following this, 20 ml of 120 mM p-nitrophenylphasphate was added as substrate and the absorbance of 405 nm was recorded using a microplate reader (Model EL309, Bio-Tek Instruments, Winooski, Vt.). The following equation was used to calculate the of alkaline phosphatase activity:

$$(od_{405}/ml)(Total\ Reaction\ Volume)$$

$$IU/ml = (18.8\ ml/mmole\ cm)(sample\ volume)$$
$$(Spectrophotometer\ path\ length)$$

A small aliquot of infectious medium and the cell pellet with the remaining medium were collected separately at 3 days p.i. and were tested individually for expression of SEAP. The cell pellets were sonicated for 20 seconds to release alkaline phosphatase from the cells. The activity of SEAP for both the medium and the cell fractions were tested under the same conditions. Percent secretion was determined by dividing the resultant SEAP activity from the medium fraction by the value of total SEAP activity.

Table 3 lists the expression levels of SEAP at six days p.i. from the different cell lines in serum free medium, following infection with the recombinant virus As-SEAP. The production of SEAP by the new cell lines was compared to Tn-5B1-4 and Sf-21 cells. Interestingly, SEAP activity from Tn-4B and Tn-4B31 infected cells was higher when compared to other cell lines, including Tn-5B1-4. However, the highest percent secretion obtained at day 3 p.i. was by the Tn-5B1-4 cells as shown in Table 4.

TABLE 4

Total SEAP expression in select *Trichoplusia ni* cell lines at 6 days post infection

| Cell Lines | SEAP IU/ml 1 | SEAP IU/ml 2 | SEAP IU/ml 3 | SEAP IU/ml 4 | Avg. IU/ml ±SE |
|---|---|---|---|---|---|
| 4A14 | 1.07 | 0.88 | 1.03 | 0.68 | 0.92 ± 0.09 |
| 4A2 | 1.13 | 1.88 | 0.97 | 1.69 | 1.42 ± 0.22 |
| 4A22 | — | 0.86 | 0.60 | 0.76 | 0.74 ± 0.07 |
| 4B | 5.12 | 4.25 | 2.36 | 2.62 | 3.59 ± 0.66 |
| 4B31 | 8.45 | 3.82 | 3.99 | 3.82 | 5.00 ± 1.20 |
| 4B42 | 2.42 | 2.47 | 0.82 | 1.35 | 1.77 ± 0.40 |
| 4B44 | 1.26 | 1.06 | 1.04 | 1.46 | 1.21 ± 0.10 |
| Sf-21 | 3.12 | 1.25 | 0.99 | 0.96 | 1.83 ± 0.48 |
| Tn-5B1-4 | 5.08 | 1.53 | 2.46 | 1.89 | 2.29 ± 0.66 |

TABLE 5

Secreted alkaline phophatase by novel *Trichoplusia ni* cell lines at 3 days post infection in serum free medium

| Cell Lines | SEAP IU/ml Medium | SEAP IU/ml Total | % Secretion |
|---|---|---|---|
| 4A14 | 0.21 | 0.79 | 26.6 |
| 4A2 | 0.31 | 0.84 | 36.9 |
| 4A22 | 0.43 | 1.00 | 43.0 |
| 4B | 1.38 | 2.26 | 61.2 |
| 4B31 | 1.55 | 2.69 | 57.6 |
| 4B42 | 0.49 | 1.77 | 27.7 |
| 4B44 | 0.69 | 1.99 | 34.2 |
| Sf-21 | 0.79 | 1.30 | 60.8 |
| Tn5B1-4 | 1.45 | 2.02 | 71.8 |

Hink et al. (1991) considered that yields in serum-free medium were equal to or better than those in serum-supplemented medium for most cell line recombinant virus combinations. Based upon our data, whereby new cell lines established in serum-free medium were evaluated, two cell lines, Tn4b and Tn4B31, proved to be good candidates for large scale production of baculovirus pesticides and recombinant proteins.

Both Tn4B and Tn4B31 were established from *Trichoplusia ni* embryos in Ex-Cell 400™ serum-free medium. These two cell lines have a fibroblast-like shape, attached to culture flask and form a cell monolayer, three to four days after subculture. They are currently subcultured twice a week at a split ratio of 1:4 to 1:5. Mild agitation (shaking) of the flasks will result in suspension of the cells from the attached monolayer before subculturing. Both cell lines have doubling times of approximately 20–24 hrs. To date Tn4B and Tn4B31 are at 118th and 116th passage, respectively. Both cell lines are susceptible to *Autograph californica* multiple nucleocapsid nuclear polyhedrosis virus (AcMNPV) and *T. ni* single nucleocapsid nuclear polyhedrosis virus (TnSNPV).

The cell line referred to as BTI-Tn4B has been deposited under the Budapest Treaty at the American Type Culture Collection and has been assigned accession number ATCC CRL 11970. The cell line referred to as BTI-Tn4B31 has been deposited under the Budapest Treaty at the American Type Culture Collection and assigned the accession number ATCC CRL 11969. The maintenance and release of the deposits shall be made in accordance with all of the provisions of the Budapest Treaty.

Accordingly, it is to be understood that the embodiments of the invention herein described are merely illustrative of the application of the principles of the invention. Reference herein to details of the illustrated embodiments are not intended to limit the scope of the claims, which themselves recite those features regarded as essential to the invention.

I claim:

1. An insect cell line established in a serum free medium from *Trichoplusia ni* egg cells which supports replication of virus in serum free medium, supports expression of protein after infection by a recombinant virus in said serum free medium, grows in said serum free medium, and retains said ability to support replication of virus and to support expression of protein, wherein said cell line is capable of expressing SEAP at a higher level than a cell line designated Tn-5B1-4.

2. The insect cell line of claim 1 wherein at least 30 occlusion bodies are produced per cell after infection by *Autographa californica* multiple nuclear polyhedrosis virus, when said cell line is cultured and inoculated by the following steps:
    a) seeding said cell line in at least one well at a density of $1 \times 10^5$ cells/ml in serum free medium;
    b) allowing said cells to attach for two to three hours;
    c) drawing off said medium from said well;
    d) adding 0.5 ml of fresh serum free medium;
    e) inoculating said cells with said virus at a multiplicity of infection of five; and
    f) measuring occlusion body production at six days post infection.

3. The insect cell line of claim 2 wherein at least 50 occlusion bodies are produced per cell after infection by *Autographa californica* multiple nuclear polyhedrosis virus.

4. An insect cell line established in a serum free medium from *Trichoplusia ni* egg cells which supports replication of virus in serum free medium, supports expression of protein after infection by a recombinant virus in said serum free medium, grows in said serum free medium, and retains said ability to support replication of virus and to support expression of protein, wherein at least 90 occlusion bodies are produced per cell after infection by *Autographa californica* multiple nuclear polyhedrosis virus, when said cell line is cultured and inoculated by the following steps:
    a) seeding said cell line in at least one well at a density of $1 \times 10^5$ cells/ml in serum free medium;
    b) allowing said cells to attach for two to three hours;
    c) drawing off said medium from said well;
    d) adding 0.5 ml of fresh serum free medium;
    e) inoculating said cells with said virus at a multiplicity of infection of five; and
    f) measuring occlusion body production at six days post infection.

5. An insect cell line established in a serum free medium from *Trichoplusia ni* egg cells which supports replication of virus in serum free medium, supports expression of protein after infection by a recombinant virus in said serum free medium, grows in said serum free medium, and retains said ability to support replication of virus and to support expression of protein, wherein at least 850 occlusion bodies are produced per cell after infection by *Trichoplusia ni* single nuclear polyhedrosis virus, when said cell line is cultured and inoculated by the following steps:
    a) seeding said cell line in at least one well at a density of $1 \times 10^5$ cells/ml;
    b) allowing said cells to attach for two to three hours;
    c) drawing off said medium from said well;
    d) adding 0.5 ml of fresh medium;
    e) inoculating said cells with said virus at a multiplicity of infection of five; and
    f) measuring occlusion body production at six days post infection.

6. An insect cell line established in a serum free medium from *Trichoplusia ni* egg cells which supports replication of virus in serum free medium, supports expression of protein after infection by a recombinant virus in said serum free medium, grows in said serum free medium, and retains said ability to support replication of virus and to support expression of protein, wherein at least 1000 occlusion bodies are produced per cell after infection by *Trichoplusia ni* single nuclear polyhedrosis virus.

7. The insect cell line of claim 1 wherein at least 175 IU/ml of expressed Beta-galactosidase is produced after infection by a recombinant *Autographa californica* multiple nuclear polyhedrosis virus expressing secreted alkaline phosphatase, when said cell line is cultured and inoculated by the following steps:
    a) seeding said cell line in at least one well at a density of $1 \times 10^5$ cells/ml;
    b) allowing said cells to attach for two to three hours;
    c) drawing off said medium from said well;
    d) adding 0.5 ml of fresh medium;
    e) inoculating said cells with said recombinant virus at a multiplicity of infection of ten;
    f) centrifuging said cells, medium and virus at 1,000×g for 1 hour;
    g) removing said medium from said centrifuged cells, medium and virus;
    h) adding 0.5 ml of fresh medium; and
    i) measuring said Beta-galactosidase production at six days post infection.

8. The insect cell line of claim 1 wherein at least 2 IU/ml of expressed alkaline phosphatase is produced after infection by a recombinant *Autographa californica* multiple nuclear polyhedrosis virus expressing secreted alkaline phosphatase, when said cell line is cultured and inoculated by the following steps:

a) seeding said cell line in at least one well at a density of $1\times10^5$ cells/ml;

b) allowing said cells to attach for two to three hours;

c) drawing off said medium from said well;

d) adding 0.5 ml of fresh medium;

e) inoculating said cells with said recombinant virus at a multiplicity of infection of ten;

f) centrifuging said cells, medium and virus at 1,000×g for 1 hour;

g) removing said medium from said centrifuged cells, medium and virus;

h) adding 0.5 ml of fresh medium; and i) measuring said β-galactosidase production at six days post infection.

9. An insect cell line established in a serum free medium from *Trichoplusia ni* egg cells which supports replication of virus in serum free medium, supports expression of protein after infection by a recombinant virus in said serum free medium, grows in said serum free medium, and retains said ability to support replication of virus and to support expression of protein, wherein said cell line has all of the identifying characteristics of the cell line deposited under the Budapest Treaty at the American Type Culture Collection and assigned the accession number ATCC CRL 11970.

10. An insect cell line established in a serum free medium from *Trichoplusia ni* egg cells which supports replication of virus in serum free medium, supports expression of protein after infection by a recombinant virus in said serum free medium, grows in said serum free medium, and retains said ability to support replication of virus and to support expression of protein, wherein said cell line has all of the identifying characteristics of the cell line deposited under the Budapest Treaty at the American Type Culture Collection and assigned the accession number ATCC CRL 11969.

* * * * *